(12) United States Patent  (10) Patent No.: US 7,408,630 B2
Nakamura et al.  (45) Date of Patent: Aug. 5, 2008

(54) RECORDED ARTICLE WITH ANTI-COUNTERFEIT MEASURES

(75) Inventors: Hiroto Nakamura, Nagano (JP); Akio Owatari, Nagano (JP); Masataka Kamijo, Nagano (JP); Yasuko Hirano, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 77 days.

(21) Appl. No.: 11/286,223

(22) Filed: Nov. 23, 2005

(65) Prior Publication Data

US 2006/0082761 A1   Apr. 20, 2006

Related U.S. Application Data

(62) Division of application No. 10/469,282, filed on Aug. 28, 2003.

(51) Int. Cl.
    *G06K 9/74* (2006.01)
(52) U.S. Cl. .......................................... 356/71; 382/190
(58) Field of Classification Search ........................ None
    See application file for complete search history.

(56) References Cited

U.S. PATENT DOCUMENTS

| | | | |
|---|---|---|---|
| 2,407,608 A | 9/1946 | Judd et al. |
| 3,789,520 A | 2/1974 | Lowi |
| 4,514,085 A | 4/1985 | Kaye |
| 4,824,144 A | 4/1989 | Tasma |
| 5,169,707 A | 12/1992 | Faykish et al. |

(Continued)

FOREIGN PATENT DOCUMENTS

CN   1132696 A   10/1996

(Continued)

OTHER PUBLICATIONS

Search Report, dated Dec. 19, 2005, from European patent appln. No. 02805472.4

(Continued)

*Primary Examiner*—Gregory J. Toatley, Jr.
*Assistant Examiner*—Juan D Valentin
(74) *Attorney, Agent, or Firm*—Stroock & Stroock & Lavan LLP (57) ABSTRACT

An object is to provide a recorded article or sticker whereby counterfeited articles and genuine articles can be visually distinguished in simple fashion in the market and wherein it is not possible to identify in the market the location and type of the anti-counterfeiting measures that have been taken. Both an overt region 3 (which can be recognized visually in the market) are printing using a color-change ink or liquid-crystal ink, for example, and a covert region 5 formed by for example optical retro-reflective printing (which cannot be recognized without using a special tool) are provided on the surface of the same recording medium. The overt region 3 and the covert region 4 may be arranged at different locations or may overlap, or may be positionally aligned. The overt letter/design pattern and the covert letter/design pattern may be the same or different. An overt recording that is printed using liquid-crystal ink may also function as a covert recording by employing a genuineness inspection method using a circularly polarized plate. A sticker may be provided with one or a plurality of cuts such that the sticker is broken when peeled off, so that it cannot be re-used.

1 Claim, 9 Drawing Sheets

U.S. PATENT DOCUMENTS

| | | | |
|---|---|---|---|
| 5,202,677 | A | 4/1993 | Parker et al. |
| 6,061,122 | A | 5/2000 | Hoshino et al. |
| 6,214,443 | B1 | 4/2001 | Palmasi et al. |
| 6,351,537 | B1 | 2/2002 | Dovgodko et al. |
| 6,993,655 | B1 | 1/2006 | Hecht et al. |
| 2002/0163678 | A1 | 11/2002 | Haines et al. |

FOREIGN PATENT DOCUMENTS

| | | |
|---|---|---|
| JP | 01-31505 Y2 | 9/1989 |
| JP | 01-31513 Y2 | 9/1989 |
| JP | 06-507737 A | 9/1994 |
| JP | 07-068981 A | 3/1995 |
| JP | 08-069680 A | 3/1996 |
| JP | 08-324169 A | 12/1996 |
| JP | 09-240134 A | 9/1997 |
| JP | 09-254520 A | 9/1997 |
| JP | 10-060303 A | 3/1998 |
| JP | 10-097208 A | 4/1998 |
| JP | 11-042875 A | 2/1999 |
| JP | 2000-1071 A | 1/2000 |
| JP | 2000-25373 A | 1/2000 |
| JP | 2001-063300 A | 3/2001 |
| JP | 3079156 U | 5/2001 |
| JP | 2001-347745 A | 12/2001 |
| WO | 97/01156 A1 | 1/1997 |
| WO | 98/10943 A1 | 3/1998 |
| WO | 00/27645 A1 | 5/2000 |
| WO | WO-00/27645 A1 | 5/2000 |
| WO | 00/62258 A1 | 10/2000 |
| WO | WO-00/62258 A1 | 10/2000 |

OTHER PUBLICATIONS

Office Action in Chinese patent application No. 02806067.9, dated May 13, 2005 (with English translation).

Taiwanese Office Action and English translation from corresponding Taiwan patent application 91136882.

Microfilm of the specifcation and drawings annexed to the request of Japanese Utility Model Application No. 4873/1984 (Laid-open No. 117182/1985) (Toppan Printing Co., Ltd.), Aug. 8, 1985.

RECORDED ARTICLE WITH ANTI-COUNTERFEIT MEASURES

CROSS-REFERENCE TO RELATED APPLICATION

This application is a division of copending application Ser. No. 10/469,282, having a § 371(c) date of Aug. 28, 2003.

TECHNICAL FIELD

The present invention relates to a recorded article such as for example a printed article, with anti-counterfeit measures.

BACKGROUND ART

In order to prevent counterfeiting of recorded articles such as for example printed articles produced by color copying technology using an optical image scanner and color printer or in order to ascertain genuineness by identifying whether a subject article is a forgery or a genuine article, recording or printing techniques are known in which special optical characteristics are applied to the surface of the printed article. Such recording techniques for preventing counterfeiting can be classified into two types, called overt and covert. The special optical characteristics of the overt technique are exposed i.e. can be identified simply by directly viewing with the naked eye under natural light. The special optical characteristics of the covert technique are hidden and can only be identified by viewing under special optical conditions or using special optical tools.

A typical example of an overt technique is recording or printing using a color-change ink; this is disclosed in Laid-open Japanese Patent Publication No. H8-324169 or Laid-open Japanese Patent Publication No. H9-254520 or Laid-open Japanese Patent Publication No. H10-060303. A color-change ink has the property that the main wavelength of reflected light therefrom when white light is directed on to the surface of the ink changes depending on the angle of incidence (angle of reflection). The perceived color of a surface printed with a color-change ink therefore changes when the angle of viewing is changed.

A typical example of a covert technique is recording or printing accompanied by surface processing to produce optical retroreflection properties, as disclosed in U.S. Pat. No. 2,407,608 or Laid-open Japanese Patent Publication No. H10-97308, for example. Optical retroreflection means a reflection characteristic whereby the angle of incidence and the angle of reflection are substantially the same i.e. a reflection characteristic in which incident light is bent back so that the reflected light is returned to the light source. A covertly recorded portion having optical retroreflection is of exactly the same color as the surrounding region when viewed under natural light and so cannot be distinguished, but can be distinguished from the surrounding region when viewed using a special tool.

Since both overt techniques and covert techniques require special inks or special processes for processing, a recorded article manufactured using such techniques cannot be reproduced using a simple color copier.

A recorded article to which an overt technique has been applied and a counterfeit article manufactured by simply copying this using a color copier can be differentiated visually simply by ordinary viewing under natural light. Accordingly, even supposing such a simple counterfeit product appears on the market, people in the market can easily notice that it is not a genuine product. The effectiveness of overt techniques in excluding simple counterfeit products from the market is therefore high. Other hand, since the location and type of such overt recording on the article in question are apparent to the eyes of anyone, this gives a clue to other persons intending to imitate such overt recording.

In contrast, the presence of covert recording cannot be noticed by people in the market. There is therefore little likelihood of clues to imitate this covert recording being given to other persons. However, people in the market cannot normally identify the presence of covert recording, so there is a high probability of people in the market being simply cheated even by simple counterfeit articles.

DISCLOSURE OF THE INVENTION

An object of the present invention is therefore to provide a recorded article or printed article with anti-counterfeiting measures whereby counterfeited articles and genuine articles can be visually distinguished in simple fashion in the market and wherein it is not possible to identify in simple fashion in the market the location and type of the anti-counterfeiting measures that have been taken.

A further object of the present invention is to provide a security label in the form of a label or sticker suitable for sticking onto for example products or product packaging, that can be employed for preventing counterfeiting of products or for ascertaining genuineness.

A recorded article according to one aspect of the present invention comprises an overt recording formed by an overt technique and a covert recording formed by a covert technique on the surface of the same recorded medium. With this recorded article, genuineness can be ascertained in simple fashion even in the market by means of the overt recording and, even if counterfeit products appear imitating the overt recording, genuineness can still be ascertained using the covert recording. Also, a synergetic effect of the overt and covert recordings is obtained in that the presence of the overt recording in this recorded article acts as a decoy making it difficult to notice the presence of the covert recording.

In a recorded article according to the present invention, it can be arranged that the overt recording and covert recording at least partially overlap. It can also be arranged to make the overt recording and covert recording of different plan design in regard to for example their shape or size. Such an arrangement makes counterfeiting even more difficult.

The overt recording may be made extremely difficult to counterfeit by forming by for example superimposing liquid-crystal ink on a color-change ink.

Also, when the overt recording and covert recording are superimposed, the covert recording may be formed by an optical retroreflection layer comprising minute transparent spheres arranged on a transparent reflecting layer. With such a construction, under natural light, the covert recording is substantially transparent or close to transparent and the overt recording therebelow can be clearly seen. When viewed under special conditions or using a special tool, the covert recording can be clearly seen.

The overt recording and covert recording can also be stacked in perfect alignment by making their plan design such as shape and size completely identical. If this is done, an even more effective decoy effect of the overt recording may be exhibited.

Also, the overt recording may be formed by superimposing liquid-crystal ink on an underlayer of a specified color, or superimposing a background region around the overt recording or superimposing liquid-crystal ink on an underlayer of different color, or may also be formed by directly employing an underlayer of the above specified color, without superimposing liquid-crystal ink thereon. In this way, the overt recording can also function as a covert recording.

In this way, ascertaining genuineness can be performed using the covert recording function, by observing this recorded article, on which a recording has been formed that functions both as an overt recording and a covert recording, using liquid-crystal ink, through for example a clockwise circularly polarized plate and anticlockwise circularly polarized plate, respectively.

A security label according to a further aspect of the present invention comprises an overt recording formed by an overt technique and a covert recording formed by a covert technique on the surface of a single recording medium and further comprises an adhesive layer whereby the security label can be stuck onto a subject article such as a product or product packaging. The overt recording is capable of producing color change depending on the angle of observation by selective reflection of light. The covert recording is capable of being identified by means of a special tool or device.

Alternatively, the overt recording may be produced using a liquid-crystal material or may be produced using a material obtained by laminating a metallic oxide layer and/or metal and thin-film mica glass layer and/or silicon oxide.

Alternatively, the covert recording may contain a material that reflects or transmits light of a specified spectral pattern with respect to infra-red light, so as to enable the genuineness thereof to be ascertained by comparing the spectral pattern of the light that is reflected or the light that is transmitted in respect of illumination with infra-red light with a spectral pattern that has been stored beforehand in a specified tool or device.

Also, the area of this security label may be no more than 8 square centimeters.

Furthermore, the security label may be provided with a cut at one or a plurality of locations such that, if an attempt is made to peel off the security label once it has been a fixed to a subject article, the security label is broken and rendered incapable of re-use.

As the method of manufacturing a security label according to the present invention, an overt recording may be printed by an overt technique and a covert recording may be printed by a covert technique printing on the surface of the same recording medium; the overt technique may be a silkscreen method.

BRIEF DESCRIPTION OF THE DRAWINGS

FIG. 10 is a cross-sectional view showing the appearance when the overt recording formed using the liquid-crystal ink shown in FIG. 8 and FIG. 9 is observed through a circularly polarized plate that transmits anticlockwise polarized light;

FIG. 11 is a cross-sectional view showing the appearance when the overt recording formed using the liquid-crystal ink shown in FIG. 8 and FIG. 9 is observed through a circularly polarized plate that transmits clockwise polarized light;

BEST MODE FOR CARRYING OUT THE INVENTION

Embodiments of the present invention are described below.

In these embodiments, in each case, an overt recording (hereinbelow, simply referred to as an "overt") formed by an overt technique and a covert recording (hereinbelow, simply referred to as a "covert") formed by a covert technique are provided on the surface of the same recording medium. For the overt recording, for example recording is employed that produces a color change depending on the angle of observation by selective reflection of light (hereinbelow turned "color-change recording").

Specifically, as a material that forms selective reflection of light, there may be mentioned by way of example a liquid-crystal material or a material obtained by laminating a metallic oxide layer, metal, mica glass or silicon oxide or other material. The desired object can be achieved by preparing such a material as a printing ink and performing printing therewith. Some description will now be given concerning selective reflection.

A liquid-crystal material (in particular a cholesteric liquid-crystal) has a structure in which the molecular arrangement is twisted little by little along the helical axis, so that the liquid-crystal as a whole forms a helical structure. As is well known, such a structure provides properties such as optical rotatory power, selective optical scattering and circular polarization dichroism. Specific examples of such materials include the BASF PALIOCOLOR (registered trademark) series. Also, a material produced by laminating a metallic oxide layer, metal, mica glass and silicon oxide (hereinbelow turned optical brightness pigment) reflects light of different wavelengths depending on the angle, due to the different refractive indices of the laminated substances and so appears to human eyes as displaying color changes. Specifically, it indicates a material obtained by grinding to a suitable size a pigment formed by laminating metallic oxide such as silicon oxide, titanium oxide, aluminum oxide or iron oxide with a base material of low transparency such as thin flakes of mica or a material obtained by grinding to a suitable size a material obtained by laminating silica and a layer that reflects light, such as a metal or a metallic oxide. A specific example thereof is PALIOCROM pigment (BASF trademark) or other materials. An ink of appropriate physical properties or performance is prepared by combining any of these materials in a manufacturing device (printing device).

Figure 1A:
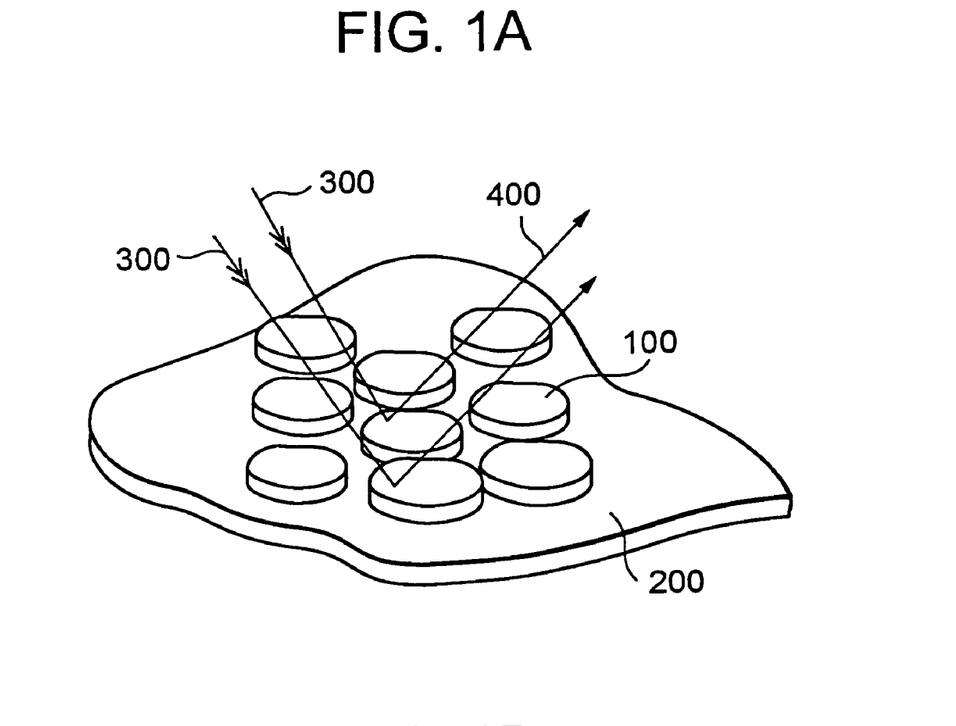
FIG. 1A and FIG. 1B are diagrams of a recording surface printed with a color-change ink using an overt technique.
Figure 1B:
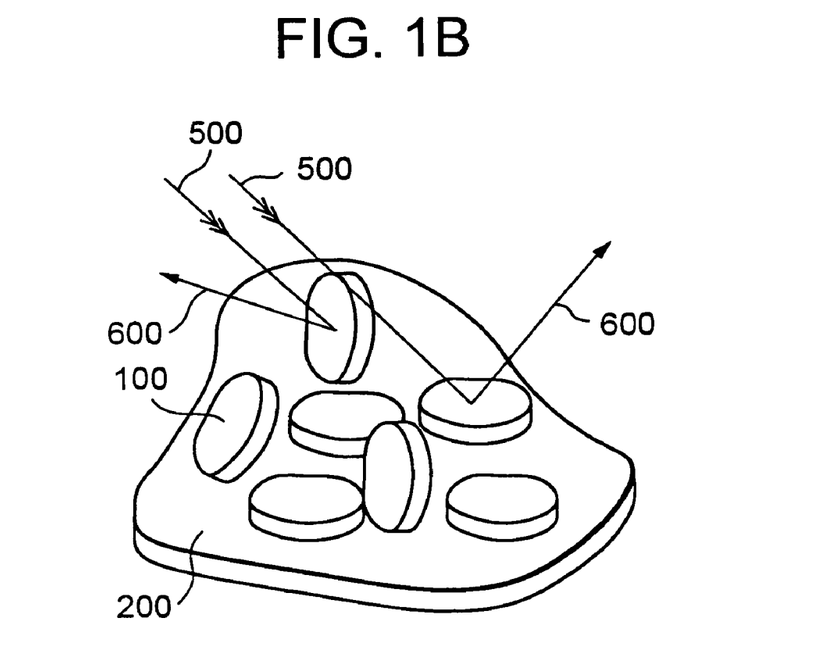

FIG. 1 is a diagram of a color-change ink recording surface.

A color-change ink can be printed by ordinary printing methods. As shown in FIG. 1A, preferably the liquid-crystal material or optical brightness pigment employed in the color-change ink consists in flat plate shapes of pigment 100 arranged in a regular attitude on the surface of a recording medium 200 for recording. As shown in FIG. 1A, by arranging the flat shapes of pigment 100 in a regular fashion, the angle of reflection of the reflected light 400 with respect to the angle of incidence of the incoming light 300 can be maintained constant. In this way, a large color change of the color-change recording can be produced, which is desirable for an overt recording. In contrast, as shown in FIG. 1B, if the flat plate shapes of pigment 100 are irregularly arranged on the surface of the recording medium 200, the reflected light 600 is reflected with scattered angles (scattered reflection) with respect to a parallel incident beam 500. With a recording surface in such a condition, the desired excellent color-change characteristic cannot be obtained.

The magnitude of the color change was described with reference to the diagrams are FIG. 1A and FIG. 1B, but when the recording surface of an actual color-change recording is observed, it is found that the condition of arrangement of the pigment is different depending on the method of printing. For example, it has been found that a method of printing using the silkscreen method is suitable for an arrangement of the flat plate shapes of pigment 100 approaching the condition of FIG. 1A.

On the other hand, in the case of a covert recording, the recording cannot be recognized solely by the naked eye under sunlight or ordinary illumination and may be adopted where recording is to be performed by a special recording method such that the recording can only be recognized using special equipment.

Specific examples that may be given include fluorescent ink or phosphorescent ink. Commercially available inks of this type may be employed. Typically, with such inks, the recording pattern emits light and may be observed by irradiating with ultraviolet light. For irradiating with ultraviolet light, for example a "black lamp" may be employed. Since the recording pattern does not emit light under sunlight or light from fluorescent lamps, it cannot be read. Such an ink may be used for printing at a position separate from the recording position of the ink used in the overt technique. Another type of covert recording that may be mentioned by way of example is recording using a recording method that produces optical retroreflection. One method of recording to produce optical retroreflection is for example to form a transparent reflective layer of a specified pattern in a given region and to spread innumerable minute transparent spheres thereon, covering this region. A covert recording (pattern of the reflective layer) recorded by such a method of producing optical retroreflection cannot be recognized visually under natural light, but can be seen if viewed for example through optical equipment capable of illuminating it with intense light from the same direction as the line of vision.

As a further covert recording technique, a recording technique may be employed such that the spectral waveform of the intensity (or optical reflectance, optical transmittance or optical absorbance thereof) of the reflected light or transmitted light therefrom when specified light is directed on to the covert recording is a specified waveform. For example, a covert recording may be employed in which recording is effected using ink containing infra-red absorbing (reflecting) material having a high absorbance (or reflectance) specifically in regard to infra-red light of wavelength of 650 nm or more. By employing such an infra-red absorbing (reflecting) ink, the genuineness of a subject article can be ascertained by comparing the spectral pattern of light reflected from the subject article on irradiation with infra-red light with the correct spectral pattern of reflected light of this infra-red absorbing (reflecting) ink, which has been stored beforehand in the inspection device. With this method of inspection, the spectral pattern of the reflected light produced by infra-red light of the infra-red absorbing (reflecting) ink is stored beforehand in the inspection device and, if it is ascertained that the spectral pattern of the reflected light from the subject article is different from the spectral pattern of the reflected light stored in the inspection device, the subject article is deemed to be a counterfeit article whereas, if it is ascertained that the spectral pattern of the reflected light from the subject article is the same as the spectral pattern of the reflected light stored in the inspection device, the subject article is deemed to be a genuine article. In order to facilitate inspection, infra-red reflecting (reflecting) ink as described above may be included in the recorded portion recorded with the overt recording technique.

Figure 2:
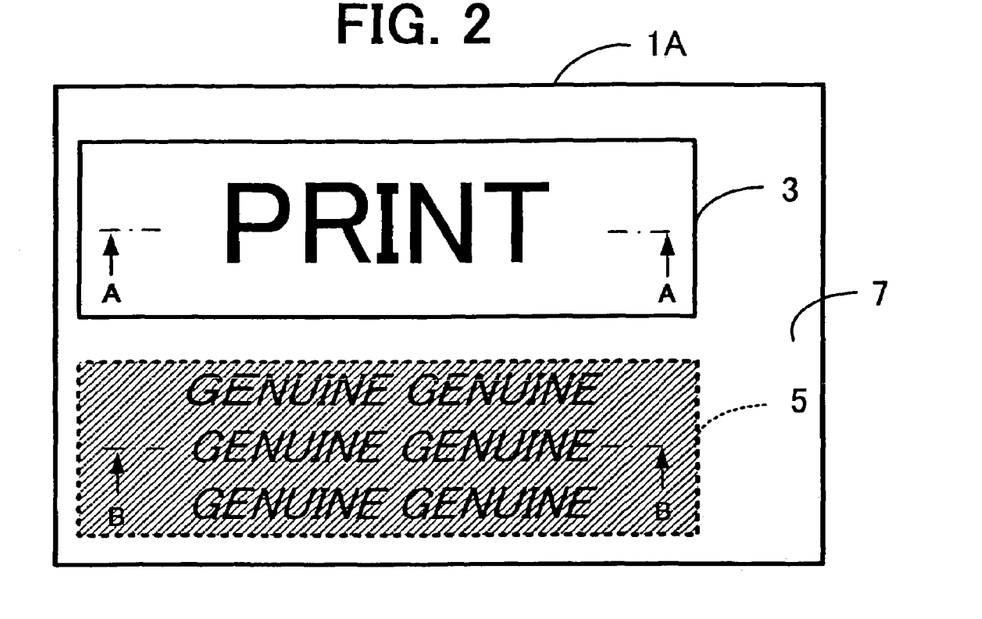
FIG. 2 is a plan view showing the plan design of major parts of an embodiment of a recorded article according to the present invention.
Figure 3:
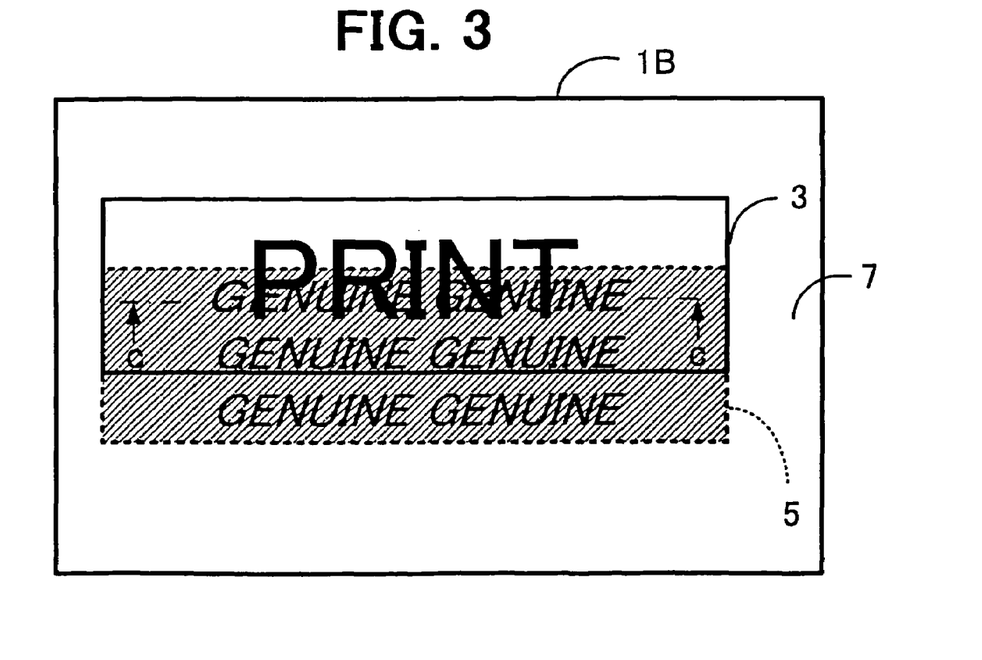
FIG. 3 is a plan view showing the plan design of major parts of another embodiment.
Figure 4:
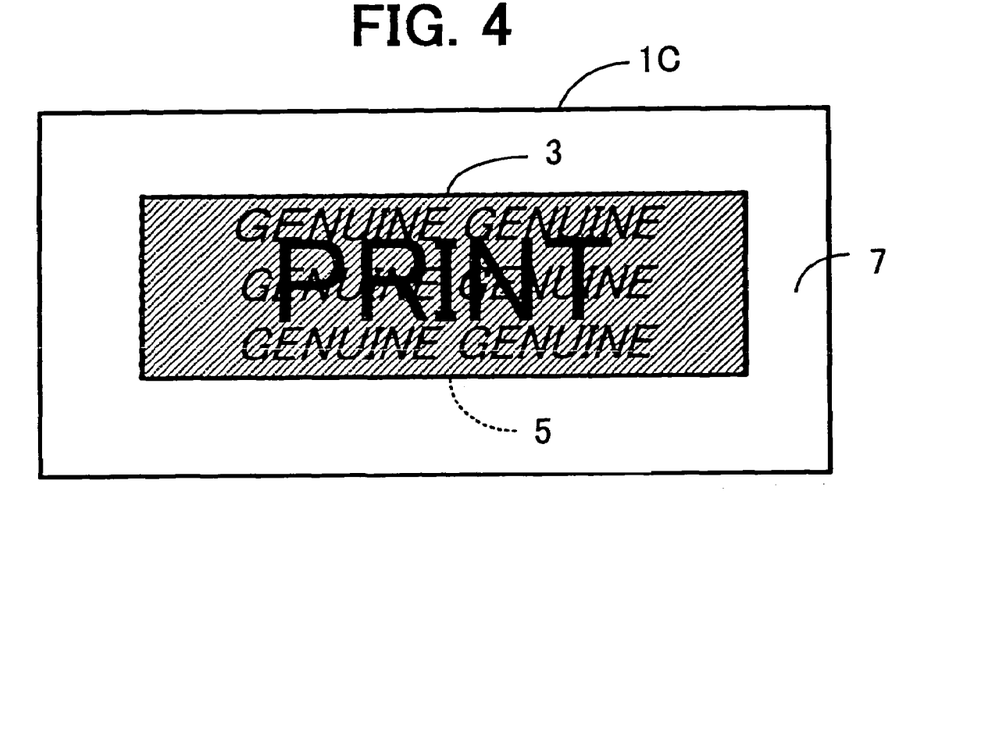
FIG. 4 is a plan view showing the plan design of major parts of a further embodiment.

FIG. 2 to FIG. 4 respectively show the plan design of major parts of three embodiments of a recorded article according to the present invention.

In the recorded articles 1A, 1B, 1C of FIG. 2 to FIG. 4, both an overt recording region 3 recorded using an overt technique and a covert region 5 recorded by a covert technique are provided on the surface of the same recording medium. In the case of the recorded article 1A of FIG. 2, the overt region 3 and covert region 5 are arranged in separate, non-overlapping locations. In the case of the recorded article 1B of FIG. 3, the overt region 3 and covert region 5 partially overlap. In the case of the recorded article 1C of FIG. 4, the overt region 3 and covert region 5 are stacked so as to be positionally aligned. Although not shown in the drawings, it is also possible to arrange one of the overt region 3 and covert region 5 so as to include the other.

In the overt regions 3 shown in FIG. 2 to FIG. 4, letters, for example "PRINT" are printed using for example a color-change ink so as to have a special optical characteristic for the overt recording. The background region other than the letters "PRINT" in the overt recording region 3 may be without the special optical characteristic for the overt recording or may be printed for example using a color-change ink of a different color, to provide another type of overt recording, which can be differentiated from "PRINT" when viewed. Also, conversely, only the background region, excluding the letters "PRINT" may be printed so as to have the special optical characteristic for the overt recording.

Consequently, it can be seen that the letters "PRINT" or the background in the overt region 3 have a special optical characteristic, for example the property that their perceived color changes depending on viewing angle, simply by viewing with the naked eye under natural light.

In contrast, in the covert region 5, for example the letters "GENUINE" are printed so as to have a special optical characteristic, for example optical retroreflection, for covert recording. The background region other than the letters "GENUINE" in the covert recording region 5 may be without the special optical characteristic for the covert recording. Also, conversely, only the background region, excluding the letters "GENUINE" may be printed so as to have the special optical characteristic for the covert recording. Whichever method is adopted, simply by viewing with the naked eye under natural light, the background region appears the same as the letters "GENUINE", so the letters "GENUINE" cannot be read.

The letters "GENUINE" in the covert region 5 can therefore be read only when viewed under special optical conditions or using a special tool; for example in the case of optical retroreflection, the letters can only be viewed when illuminated with light that is more intense than the background light, from the same direction as the line of view.

Furthermore, the covert region 5 and the background region 7 around the outside of this appear the same when viewed merely with the naked eye under natural light, so these two cannot be distinguished. It is therefore normally not possible to tell whether or not a covert region 5 is present on the recorded article 1 and where it is present on the recorded article 1.

In the recorded article having both overt and covert recordings shown in FIG. 2 to FIG. 4, genuineness can be ascertained in a simple manner even in the market, using the overt recording but even if counterfeit articles should appear imitating even the overt recording, genuineness can still be ascertained using the covert recording.

In addition, the presence of the overt recording acts as a decoy to the counterfeiter, hiding the presence of the covert recording even more effectively i.e. the overt and covert recordings may be regarded as having a synergetic effect. That is, there is a stronger probability than in the case of prior art articles, in which only a covert recording is employed on its own, that the counterfeiter, noticing the presence of the overt recording, may not anticipate the presence of a covert recording and may therefore be neglectful of efforts to search for a covert recording.

Furthermore, the presence of both overt and covert recordings together on the same recorded article makes counterfeiting itself extremely difficult. Specifically, in fact, in the case of both overt and covert recordings, even when these are employed alone, special inks or special methods of manufacture are necessary in order to imitate these exactly, so this is not easy because of the high cost. In these circumstances, the presence of both overt and covert recordings on the same recorded article requires an even more complex and high-cost method of manufacture, so counterfeiting to produce an exact imitation is extremely difficult. In particular, when, as shown in FIG. 3 and FIG. 4, the overt and covert recordings overlap, in this overlapping portion, the optical characteristics of both the overt and covert recordings act in combination, so elucidation of the materials and/or structure of this portion is extremely difficult for the counterfeiter; even if the counterfeiter knows these, it is difficult to achieve the same color tone or optical conditions, so, as a result, an exact imitation is very difficult.

The plan design (i.e. the external shape and size of the regions themselves and the shape, size and arrangement and other particulars of the letters or designs recorded in the regions) of the overt region 3 and covert region 5 shown in FIG. 2 to FIG. 4 can be freely determined. However, in a preferred embodiment, as in the examples of FIG. 2 to FIG. 4, the patterns of the overt region 3 and covert region 5 are different in regard to for example the size or type or arrangement of the letters or designs. Such differences of pattern make manufacture of a counterfeited articles difficult due to the added complexity.

Furthermore, regarding the arrangement of the covert region 3 and covert region 5, if these two regions are superimposed as described above, the advantage is obtained that the method of manufacturing counterfeits becomes extremely difficult. On the other hand, if the overt region 3 and the covert region 5 are arranged in completely different locations, the advantage is obtained that it is difficult to discover the covert recording. In particular, if for example the overt recording is a large striking pattern whereas the covert recording is a small pattern arranged in a location that cannot easily be discovered, the decoy effect of the covert recording is exhibited to even more advantage, so that the covert recording is even more difficult to discover.

Furthermore, a plurality of variations in regard to the arrangement and/or patterns of the overt and covert recordings described above may be employed in suitable combination, thereby further improving difficulty of counterfeiting.

Figure 5:
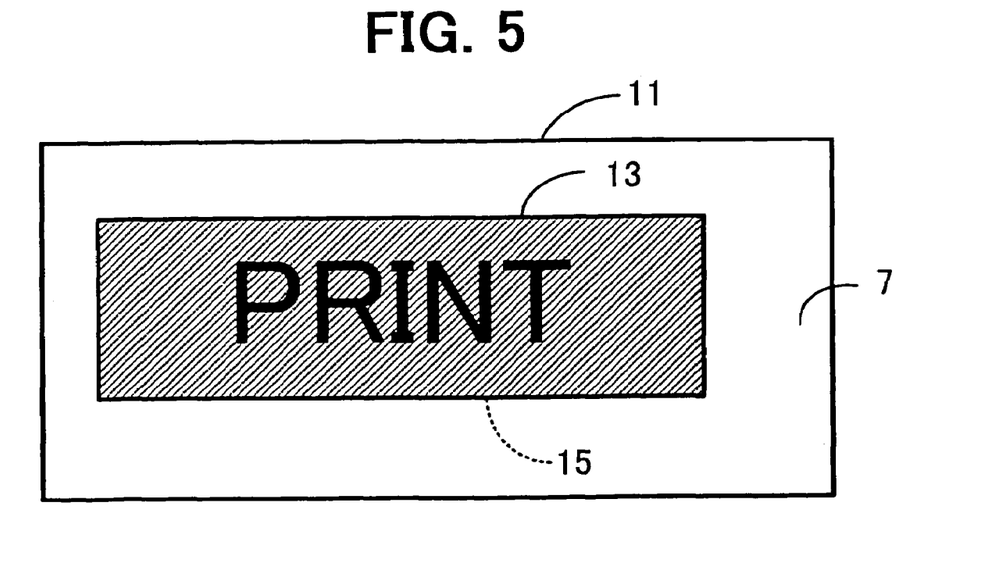
FIG. 5 is a plan view showing the plan design of major parts of yet a further embodiment.

FIG. 5 shows a plan design of major parts of another embodiment of a recorded article according to the present invention.

In the recorded article 11 shown in FIG. 5, an overt region 13 and covert region 15 having exactly the same plan design are made to be aligned in position. Specifically, in these regions 13 and 15, for example the letters "PRINT" have the special optical characteristics of the overt recording and also have the special optical characteristics of the covert recording, while the background area apart from the letters "PRINT" does not have these special optical characteristics or, conversely, only the background area, excluding the letters "PRINT" has both of the special optical characteristics of the overt and covert recordings. Alternatively, the letters "PRINT" may have the special optical characteristics of the overt recording while the background area has the special optical characteristics of the covert recording; or conversely.

In this way, even when overt and covert recordings of the same plan design are aligned in position, the decoy effect of the overt recording is effectively exhibited, hiding the presence of the covert recording. That is, there is a high probability that the counterfeiter will assume that the overt region 13 consists solely of an overt recording and will not expect this to be combined with a covert recording. As a modified example, the overt and covert recordings of the same plan design may overlap, but shifted by a slight distance (for example a distance smaller than the line thickness of the letters), or overt and covert recordings of similar plan designs differing somewhat in size may be stacked in a concentric positional relationship.

Figure 6:
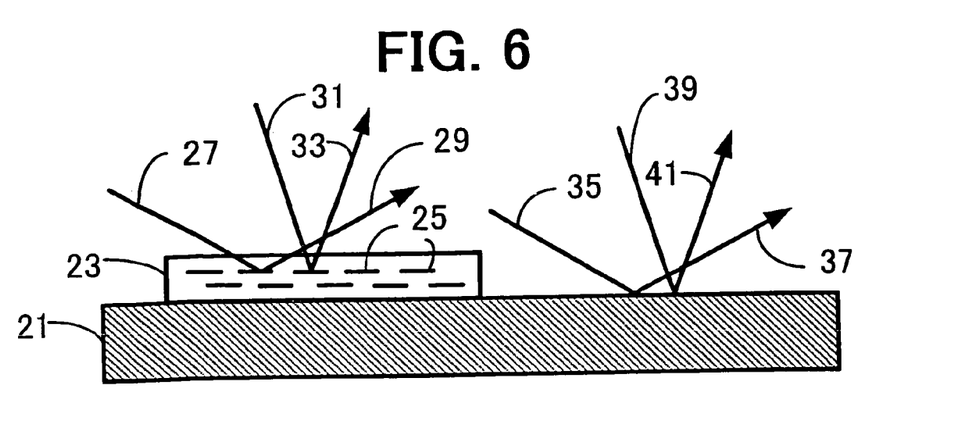
FIG. 6 is a cross-sectional view showing an example of the construction of a base portion of the cross-section, (for example, cross-section along the line A-A of FIG. 2) of an overt region 3 of the printed article shown in FIG. 2 or FIG. 3.

FIG. 6 shows an example of the structure of the base portion of the cross-section (for example the cross-section A-A of FIG. 2) of an overt region 3 of the recorded article shown in FIG. 2 or FIG. 3.

As shown in FIG. 6, the pattern of letters or design of the overt recording (for example "PRINT") is printed with color-change ink 23 on the upper surface of the base 21. For the color-change ink 23, there may be employed for example a color-change ink obtained by mixing flat pigment shapes 25 comprising for example a liquid-crystal material or optical brightness pigment with ordinary ink. Printing using the color-change ink 23 may be performed by a special printing method in which the surface directions of the surfaces 25 of the flat pigment shapes are aligned, for example by the silk-screen method.

Light which is incident onto the surface of the color-change ink 23 exits as reflected light that is reflected by the internal flat pigment shapes 25. When this happens, specified wavelengths are selectively emphasized by interference of the reflected light at the upper surface and the reflected light at the lower surface of the flat pigment shapes 25. The wavelengths that are emphasized change depending on the angle of incidence. Accordingly, as shown in FIG. 6, when for example beams of white light 27, 31 are incident at different angles of incidence, the respective reflected beams 29 and 33 appear to have different colors. Consequently, the area that is printed with the color-change ink 23 appears in a different color depending on the angle of view. In contrast, the reflected beams 37, 41 of the white light beams 35 and 39 that are incident on areas that have not been specially printed in this way are all of the same color, so there is no color change depending on angle of view.

Figure 7:
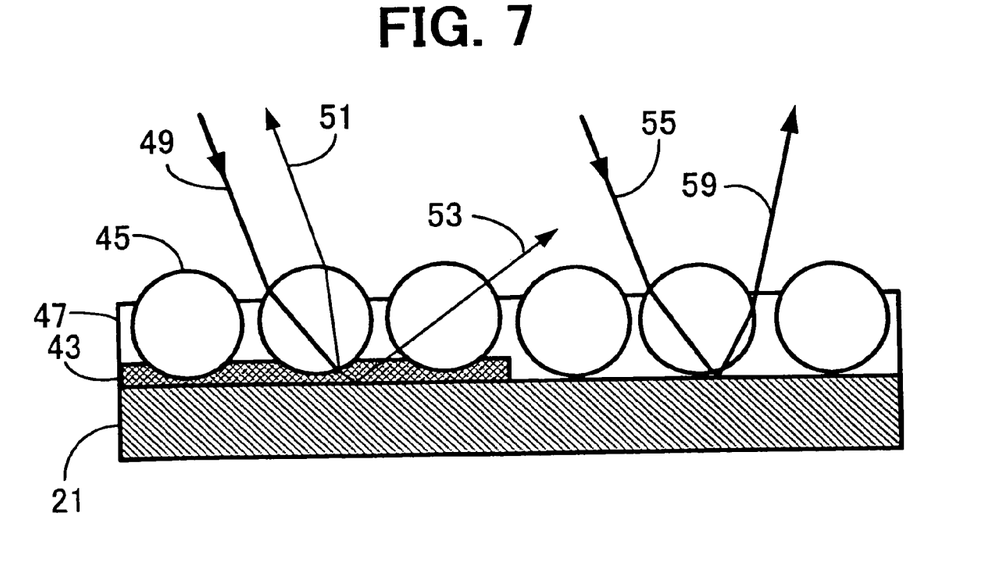
FIG. 7 is a cross-sectional view showing an example of the construction of a base portion of the cross-section, (for example, cross-section along the line B-B of FIG. 2) of a covert region 5 of the printed article shown in FIG. 2 or FIG. 3.

FIG. 7 shows an example of the structure of the base portion of the cross-section (for example, cross-section along the line B-B of FIG. 2) of the covert region 5 of the recorded article shown in FIG. 2 or FIG. 3.

The example shown in FIG. 7 is an example in which a covert recording is constituted by a recording method in which optical retroreflection is conferred thereon. As shown in FIG. 7, a transparent reflective layer 43 is formed with letters or a design pattern (for example, "GENUINE") of the covert recording on the upper surface of the base 21. On top of this, innumerable minute transparent spheres 45 are spread so as to cover the entire covert region 5 and are then fixed by an adhesive layer 47.

Part of the upper surface below the minute spheres 45 above the reflective layer 43 is covered by a reflective layer 43. By selection of the material of the reflective layer 42, minute spheres 45 and adhesive layer 47, reflection of light that has passed through the interior of the minute spheres 45 at the upper surface where the minute spheres 45 are in contact with the reflective layer 43 may be facilitated or, on the other hand, substantially all of the light that has passed through the interior of the minute spheres 45 may be arranged to exit to outside the minute spheres 45 without being reflected at the surface where the minute spheres 45 make contact with the adhesive layer 43.

When light is incident on a covert region 5 constructed in this way, the light 49 that is incident on the region where the reflective layer 43 is present enters the minute spheres 45, so part thereof is reflected at the surface of the minute spheres 45, producing retroreflection light 51 that returns in the direction of the incident light 49. Part of the remainder of the incident light 49 is reflected at the surface of the base 21 after exiting to the minute spheres 45 and exits in a direction (diffuse reflected light 53) completely different from that of the incident light 49. Also, the light 55 that is incident in the region where the reflective layer 43 is not present enters the minute spheres 45, so substantially all of this light is reflected at the surface of the base 21 after exiting the minute spheres 45 and exits in a direction completely different from that of the incident light 55 (diffuse reflected light 59).

Consequently, under natural light that is incident with substantially the same intensity from all directions, the retro-reflected light 51 does not stand out, since it is mixed with other diffuse reflected light, so the covert recording cannot be recognized with the naked eye. However, if the covert region 5 is illuminated with intense light from the same direction as the line of vision, the amount of light of the retro-reflected light 51 becomes larger than the diffuse reflected light 53, so the covert recording can be seen.

Figure 8:
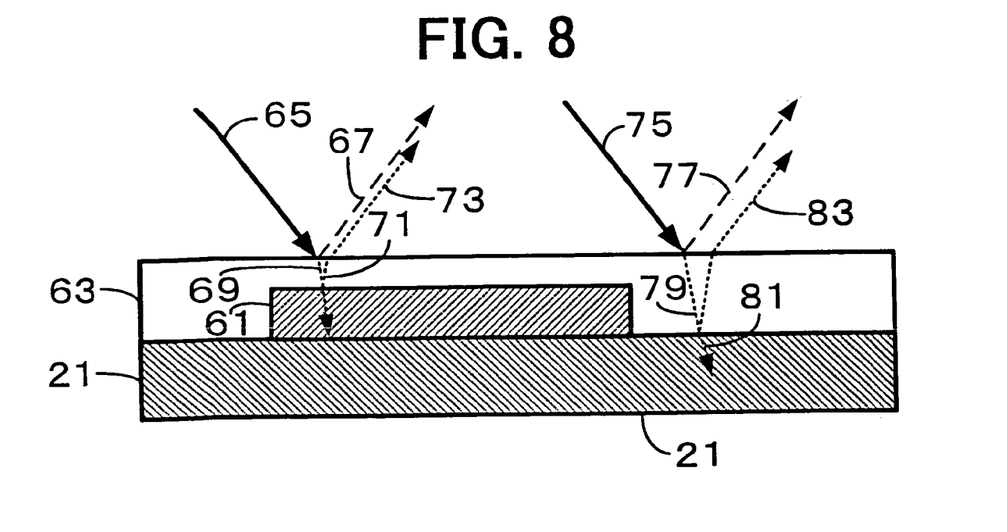
FIG. 8 is a cross-sectional view showing a further example of the construction of the cross-section of an overt region 3 of the printed article shown in FIG. 2 or FIG. 3.

FIG. 8 shows an example of another structure of the cross-section of the overt region 3 of the recorded article shown in FIG. 2 or FIG. 3.

In the example shown in FIG. 8, an overt recording is formed using liquid-crystal ink. As shown in FIG. 8, letters or a design pattern (for example "PRINT") of the overt recording are printed with a specified ink 61 on the up per surface of the base 21. On top of this, liquid-crystal ink 63 having circular polarization dichroism is used to coat the entire overt region 3. As the specified ink 61, an ordinary colored ink may be employed, or a color-change ink as described above may be employed or a liquid-crystal ink may be employed (in this case, the liquid-crystal ink is laminated). As the liquid-crystal ink 63, a cholesteric liquid-crystal ink (for example BASF's PALIOCOLOR (registered trademark)) having optical properties such as optical rotator power, selective optical scattering and circular polarization dichroism may be employed.

When light is incident on an overt region 3 constituted in this way, the light 65 that is incident on the region of the specified ink 61 is divided into two circularly polarized beams, anticlockwise beam 67 and clockwise beam 69, by the circular polarization dichroism of the liquid-crystal ink 63; the anticlockwise beam 67 is reflected by the liquid-crystal ink 63, while the clockwise beam 69 is transmitted through the liquid-crystal ink 63. When the clockwise beam 69 that has thus been transmitted is incident on the specified ink 61, part thereof 71 is absorbed while the remaining part (having the color of the specified ink 61) 73 is reflected. Consequently, the color obtained by combining the anticlockwise beam 67 reflected by the liquid-crystal ink 63 and the clockwise beam 73 reflected by the specified ink 61 is observable by human beings.

In contrast, in the region where no specified ink 61 is present, the light 75 that is incident in the region where for example the base 21 can be seen is split into two circularly polarized beams, anticlockwise beam 77 and clockwise beam 79, in the same way as described above, due to the circular polarization dichroism of the liquid-crystal ink 63, the anticlockwise beam 77 being reflected by the liquid-crystal ink 63 and the clockwise beam 79 being transmitted through the liquid-crystal ink 63. The transmitted clockwise beam 79 is incident on the base 21, where part thereof 81 is absorbed and the remaining part (having the color of the base 21) 83 is reflected. Consequently, the color obtained by combining the anticlockwise beam 77 reflected by the liquid-crystal ink 63 and the clockwise beam 73 reflected by the base 21 is observable by human beings.

Since the color of the specified ink 63 and the color of the base 21 are different, the color that is observed by human beings is different in the region of the specified ink 63 and of the base 21. Furthermore, this observed color is not a simple color but rather is a color having a special optical effect due to the action of the liquid-crystal ink 63. For example, if the specified ink 63 is black, a rainbow-colored effect appears in the color that is seen. Also, if the specified ink 63 is a color-change ink, the color that is seen is tinged with this color-change effect. Also, if the specified ink 63 is a liquid-crystal ink, a mirror effect appears. On the other hand, if the base 21 is for example white, a pearl color effect appears in the color that is seen. In all cases, the color having a special effect obtained by the liquid-crystal ink 63 cannot be reproduced by a simple color copier.

Figure 9:
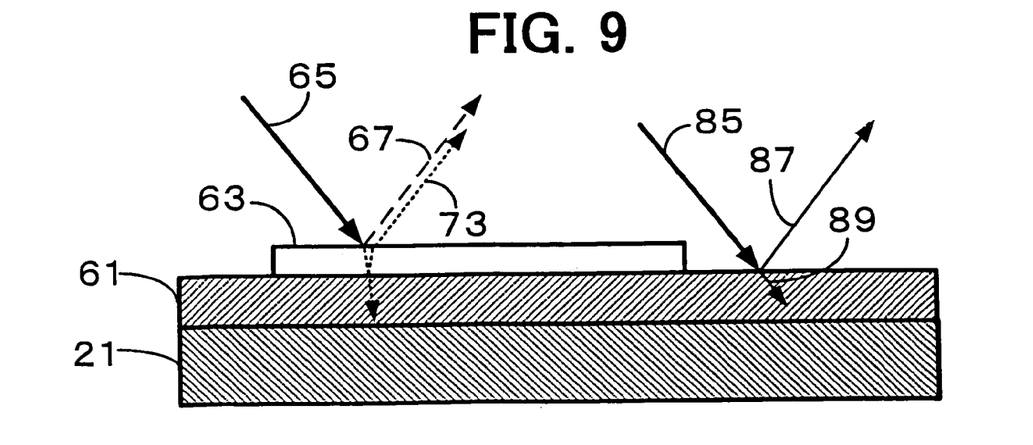
FIG. 9 is a cross-sectional view showing yet a further example of the construction of the cross-section of an overt region 3 of the printed article shown in FIG. 2 or FIG. 3.

FIG. 9 is yet a further example construction of the cross-section of the overt region 3 of the recorded article shown in FIG. 2 of FIG. 3.

The example of FIG. 9 is also an example in which an overt recording is formed using liquid-crystal ink. As shown in FIG. 9, first of all, a coating of the specified ink 61 is applied to the entire overt region 3 on the upper surface of the base 21. On top of this, an overt pattern of for example letters or a design (for example "PRINT") is printed with liquid-crystal ink 63 having circular polarization dichroism.

When light is incident onto the overt region 3 constructed as above, in the region printed with the liquid-crystal ink 63, as already described, a color having a special effect obtained by combining the anticlockwise beam 67 reflected by the liquid-crystal ink 63 and the clockwise beam 73 reflected by the specified ink 61 is observed by human beings. In contrast, in the region where there is no liquid-crystal ink 63, reflected light 67 of the color of the specified ink 61 is observed.

It should be noted that the construction shown in FIG. 8 and the construction shown in FIG. 9 could be combined. Specifically, an overt region could be designed by combining three types of pattern, namely, a pattern printed by overlaying a liquid-crystal ink 63 onto the specified ink 61, a pattern in which printing is effected only with the specified ink 61 and a pattern printed with the liquid-crystal ink 63 overlaying the base 21.

Furthermore, the overt recording formed using the liquid-crystal ink shown in FIG. 8 and FIG. 9 also has the function of a covert recording, due to the circular polarization dichroism possessed by the liquid-crystal ink. This will be described with reference to FIG. 10 and FIG. 11.

Figure 10:
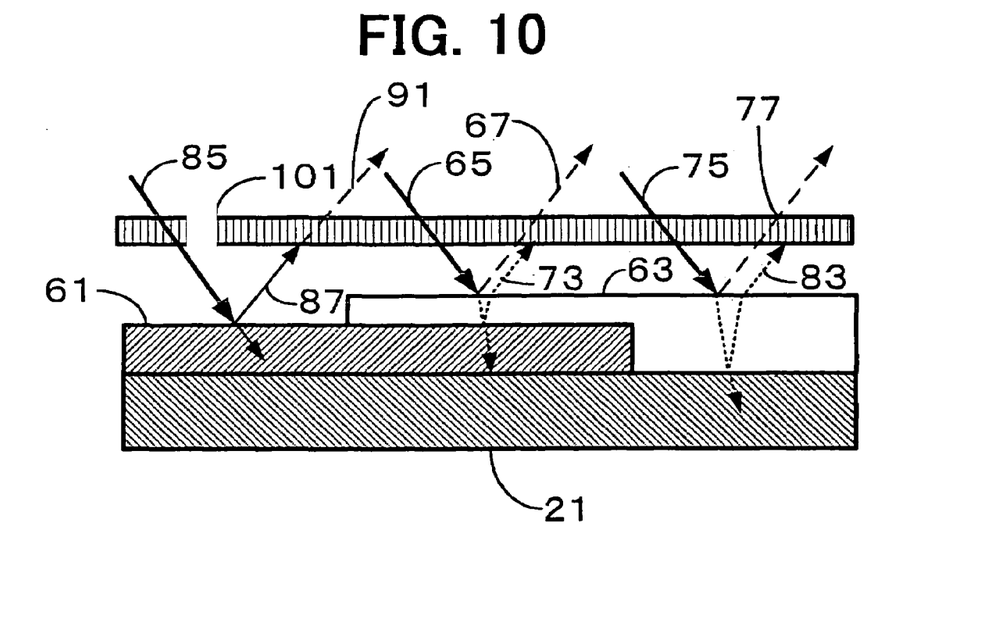
Figure 11:
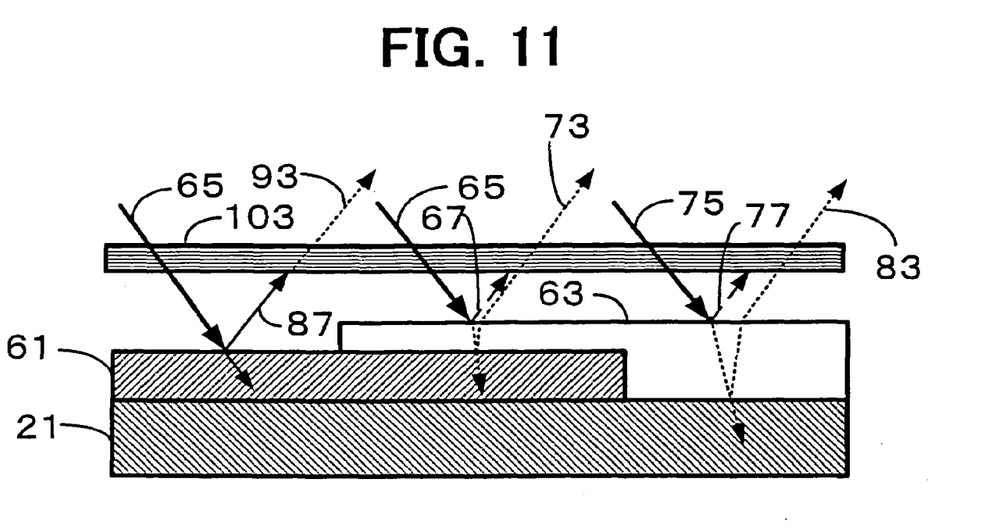

FIG. 10 describes the appearance of an overt region formed using liquid-crystal ink 63 when viewed through an anti-clockwise circular polarization plate 101 that selectively transmits anticlockwise light. FIG. 11 shows the appearance of an overt region formed using liquid-crystal ink 63 when viewed through a clockwise circular polarization plate 103 that selectively transmits clockwise light.

As shown in FIG. 10, when viewed through the anticlockwise circular polarization plate 101, of the reflected beams 67, 73, 77, 83 incoming from the region coated with liquid-crystal ink 63, only the anticlockwise beams 67 and 77 reflected by the liquid-crystal ink 63 are observed on passage through the anticlockwise circular polarization plate 101. Consequently, the region coated with the liquid-crystal ink 63 appears in the same color irrespective of the optical characteristics of the underlying layer (for example whether this consists of the specified ink 61 or the base 21). That is, the pattern that is printed with the specified ink 61 in the region coated with the liquid-crystal ink 63 cannot be seen. However, the region that is coated with the liquid-crystal ink 63 and the region that is not thus coated (region where the reflected light 87 is directly incoming from the specified ink 61) can be distinguished by different colors.

Contrast, as shown in FIG. 11, when viewed through the clockwise circular polarization plate 103, of the reflected beams 67, 73, 77, 83 incoming from the region coated with the liquid-crystal ink 63, only the clockwise beams 73 and 83 that are reflected by the underlayer after passing through the liquid-crystal ink 63 are observed through the anticlockwise circular polarization plate 103. Consequently, in the region coated with the liquid-crystal ink 63, the pattern printed with the specified ink 61 and the pattern which is not thus printed can be clearly distinguished. However, the pattern of the specified ink 61 that is coated with the liquid-crystal ink 63 and the pattern of the specified ink 61 that is not thus coated appear with the same color through the clockwise polarization plate 103 and so cannot be distinguished.

Thus, when the overt region in which the liquid-crystal ink was employed is observed using the circular polarization plates, a different appearance is presented to that seen simply with the naked eye. Consequently, even if a counterfeiter has imitated by another method the covert region using the liquid-crystal ink (it is in fact possible to produce a rainbow-colored effect or pearl colored effect and the like similar to that of a liquid-crystal ink by other methods), the fact that the article is counterfeit can still be ascertained by observation using a circularly polarized plate. In this respect, the overt recording using the liquid-crystal ink also provides the function of a covert recording. For example, if a pattern as shown in FIG. 5 is manufactured using liquid-crystal ink, it can naturally be manufactured in overt form and covert form.

A circularly polarized plate can be created for example as follows. Specifically, a PVA film or the like is uniaxially extended and dyed with iodine. If required, dyeing may be performed with another material of desired color. In addition, a protective layer is applied to prevent the iodine escaping. A circularly polarized plate is created by superimposing a ¼ wavelength film and the above film. The distinction between clockwise polarization and anticlockwise polarization plates is achieved by sticking on a linearly polarized plate and a ¼ wavelength film at an angle offset by 45° with respect to the axis of linear polarization.

Figure 12:
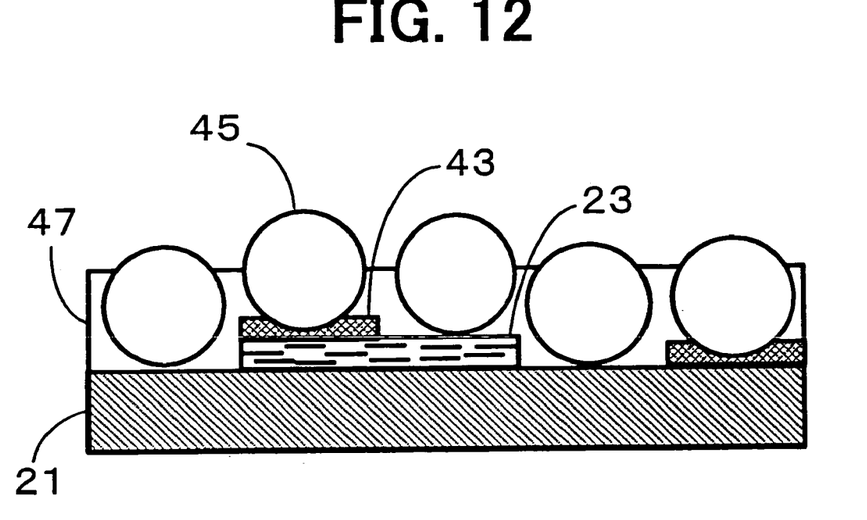
FIG. 12 is a cross-sectional view showing an example of the construction of a base portion of the cross-section of a region where the overt region and covert region shown in FIG. 3 to FIG. 5 are superimposed (for example the cross-section along C-C shown in FIG. 3)

FIG. 12 shows an example of the structure of the base portion of the cross-section (for example, cross-section along C-C shown in FIG. 3) of a region where the overt regions 3, 13 shown in FIG. 3 to FIG. 5 and the covert regions 5, 15 overlap.

As shown in FIG. 12, first of all, an overt letter or design pattern is printed with color-change ink 23 on the surface of the base 21. On top of this, a covert letter or design pattern is formed by a reflective layer 43. On top of this, innumerable minute spheres 45 are spread so as to cover the entire covert region, and fixed by means of an adhesive layer 47.

With such a region of overlapping overt and covert recordings constructed in this way, the retro-reflected light produced by the minute spheres 45 and reflective layer 43 is not noticeable under natural light, so only the overt recording produced by the color-change ink 23 can be recognized; this appears to change in color depending on the angle of view. However, when this is illuminated with intense light from the same direction as the line of view, the intensity of the retro-reflected light described above is relatively increased, with the result that the covert recording also becomes visible.

Figure 13:
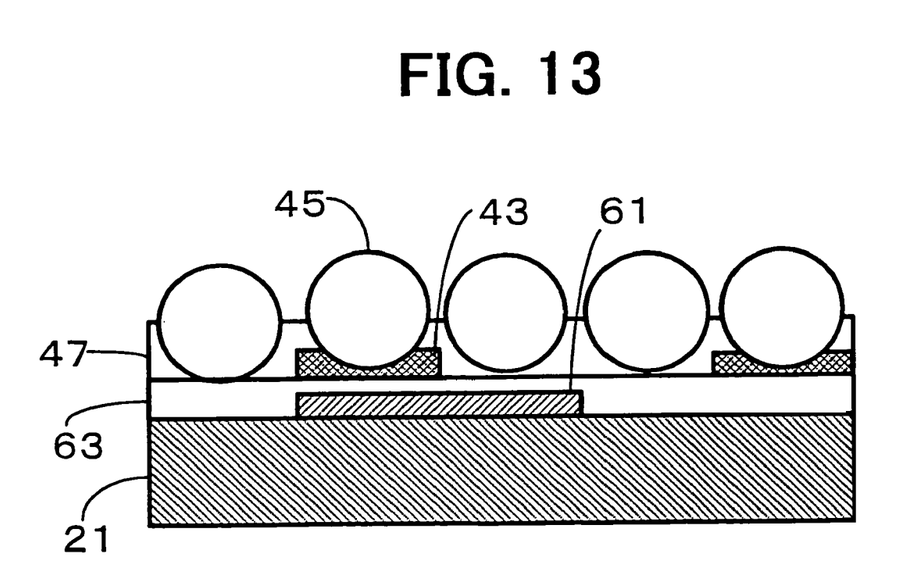
FIG. 13 is a cross-sectional view showing a further example of the construction of the cross-section of a region where the overt region and covert region shown in FIG. 3 to FIG. 5 are superimposed.

FIG. 13 shows another example of the construction of the cross-section of a region (for example, a cross-section along C-C shown in FIG. 3) where the overt and covert recordings shown in FIG. 3 and FIG. 5 overlap.

As shown in FIG. 13, first of all, an overt pattern constituted for example by letters or designs is printed with a specified ink 61 (usually, for example, colored ink, color-change ink or liquid-crystal ink) on the surface of the base 21. On top of this, the entire overt region is coated with liquid-crystal ink 63. On top of this, a covert letter or design pattern is formed by a reflective layer 43. On top of this, innumerable minute spheres 45 are spread so as to cover the entire covert region, and fixed by means of an adhesive layer 47.

With such a region of overlapping overt and covert recordings constructed in this way, the retro-reflected light produced by the minute spheres 45 and reflective layer 43 is not noticeable under natural light, so the overt recording (pattern printed with the specified ink 61) covering the liquid-crystal ink 63 is seen with a color having a special optical effect. When illuminated with intense light from the same direction as the line of view, the intensity of the retro-reflected light described above is relatively increased, with the result that the covert recording (pattern of the reflective layer 43) also becomes visible.

FIG. 14 to FIG. 17 show respectively plan views of different embodiments of a security label according to the present invention.

The security labels are stickers having an adhesive layer on one face thereof and are employed by sticking onto a subject article (for example various types of product) itself or a package of the subject articles with the aim of protecting these from counterfeiting. Overt and covert recordings are made on the face on the opposite side to the adhesive layer of these security labels. The manufacturing cost of sticking a sticker on which overt and covert recordings are made onto the surface of a subject article or packaging may be lower than that of making overt and covert recordings on the surface of the subject article itself or the packaging itself. It is desirable that a re-use prevention function should be provided so that it is not possible to peel off such security labels once they have been stuck onto a subject article and this has been sold in the market, in order to stick the label on again onto a counterfeit product. In order to prevent re-use, for example, the adhesive strength or adhesive capability of the adhesive layer is determined such that once the label has been peeled off the adhesive force is substantially eliminated. As the adhesive employed in the adhesive layer, there may be mentioned by way of example adhesives of the type in which a resin having for example an acrylic resin-based or epoxy-based skeleton is dissolved in a solvent and oxidative polymerization of the resin constituents is produced by drying the solvent. Alternatively, in order to prevent re-use, for example one or a plurality of cuts may be provided in the security label such that if an attempt is made to peel off the security label from the subject article or packaging, the security label is broken or torn. These cuts may be set at will in accordance with the size or shape of the label.

As the area of such a security label, there may be mentioned by way of example an area of no more than 8 square centimeters. With a security label of such a small size, there is little risk of impairing the external design of the subject article or packaging of the subject article onto which this label is affixed, the manufacturing costs of the label can be kept low and the step of sticking it onto the subject article presents no difficulties.

Figure 14:
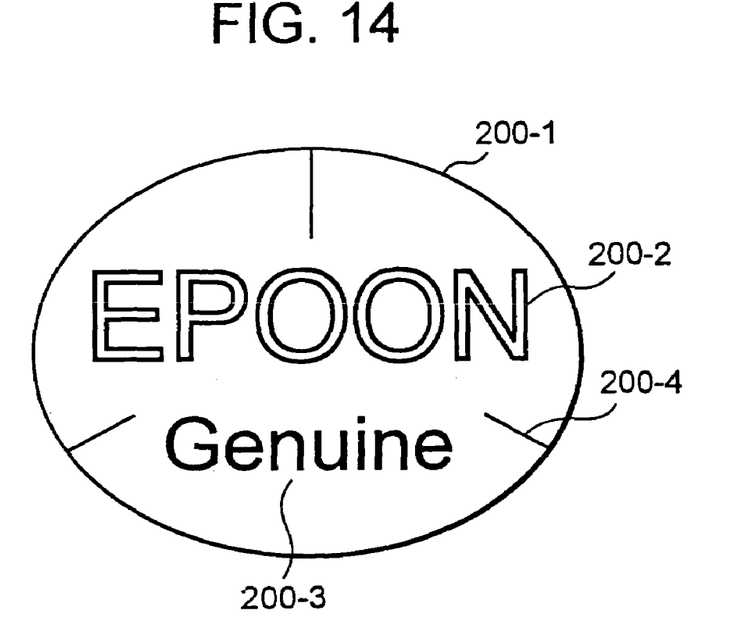
FIG. 14 is a plan view of an embodiment of a security label according to the present invention.

The security label 200-1 shown in FIG. 14 is a circular sticker of radius for example 15 mm. The portion 200-2 of the letters "EPOON" on the surface of this security label 200-1 is an overt recording recorded with color-change ink using for example a liquid-crystal material. This overt recording 200-2 is printed by for example a silkscreen method printing device. The portion of 200-3 of the letters "Genuine" designated in the Figure with the broken line is a covert recording printed with an offset type printing device using for example fluorescent ink. This covert recording 200-3 employing fluorescent ink cannot be recognized simply with the naked eye under natural light and can only be recognized when illuminated with ultraviolet rays using "black light".

An adhesive layer, not shown, is provided on the back face of this security label 200-1. This security label 200-1 is provided with cuts 200-4 directed from the outer edge towards the interior at for example three locations. The length of these cuts 200-4 is for example about ½ of the radius of this security label 200-1. When an attempt is made to peel off this security label 200-1 once it has been stuck on to for example a subject article or the packaging thereof, the security label breaks at the location of the cut 200-4, making re-use impossible.

Figure 15:
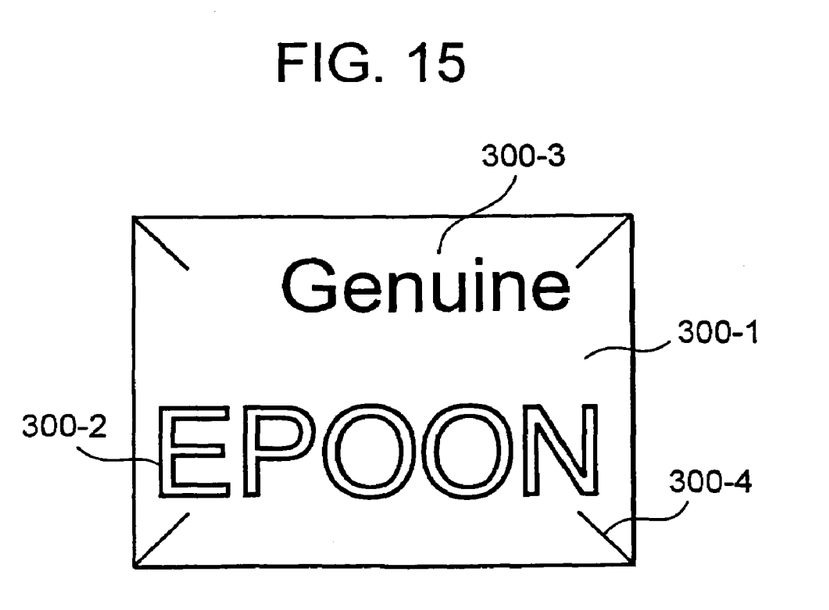
FIG. 15 is a plan view of a further embodiment of a security label according to the present invention.

The security label 300-1 shown in FIG. 15 is a rectangular sticker of for example height 20 mm, width 40 mm. The portion 300-2 of the letters "EPOON" on the surface of this security label 300-1 is an overt recording printed by the silkscreen method using ink containing for example optical brightness pigment. The ink that is used for the printing of this covert recording 300-2 contains infra-red absorbing material (for example material whose optical absorbance in the wavelength band of 650 nm or more is particularly higher than that in other wavelength bands). Consequently, when specified light containing infra-red light is directed on to this covert recording 300-2, reflected light having a specified spectral waveform is obtained and the spectral waveform of this reflected light can be checked using a special inspection device in which this spectral waveform pattern is previously stored. This overt recording 300-2 therefore functions as a covert recording. Also, the portion 300-3 of the letters "Genuine" illustrated by the broken line is a covert recording printed by offset printing using for example phosphorescent ink. This covert recording 300-3 employing phosphorescent ink cannot be recognized simply with the naked eye under natural light and can only be recognized for example when illuminated with ultraviolet rays using "black light". An adhesive layer, not shown, is provided on the back face of this security label 300-1. Cuts 300-4 are provided as shown at the four corner portions of this security label 300-1 so as to break when the security label is peeled off.

Figure 16:
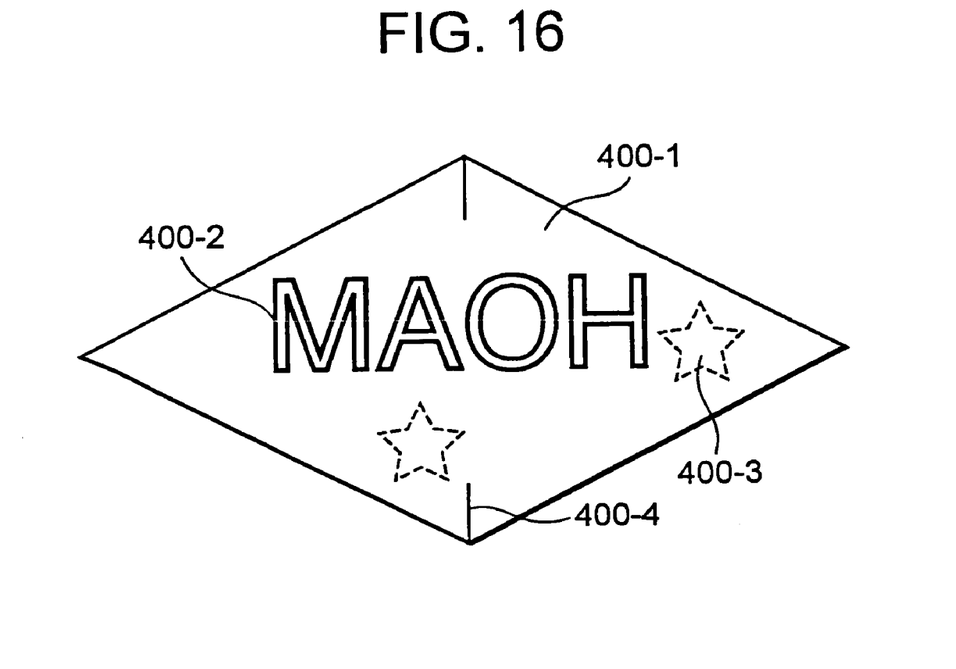
FIG. 16 is a plan view of yet a further embodiment of a security label according to the present invention.

The security label 400-1 shown in FIG. 16 is a diamond-shaped sticker of area for example 6 square centimeters. The portion 400-2 of the letters "MAOH" on the surface of this security label 400-1 is an overt recording recorded with a color-change ink containing for example liquid-crystal material. This overt recording 400-2 is printed with for example a silkscreen method printing device. Also, for example a star-shaped design portion 400-3 indicated by broken lines is a covert recording printed with an offset type printing device using for example fluorescent ink. This covert recording 400-3 can only be recognized by viewing under illumination with ultraviolet light using for example "black light". An adhesive layer, not shown, is provided on the back face of this security label 400-1. In addition, cuts 400-4 are provided as shown at two corner portions of this security label 400-1.

Figure 17:
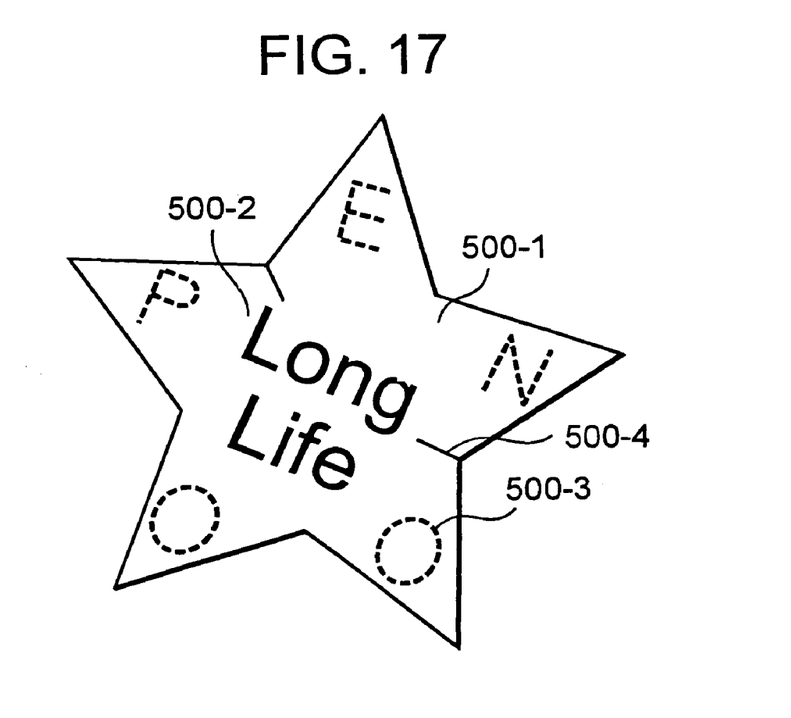
FIG. 17 is a plan view of yet a further embodiment of a security label according to the present invention.

The security label 500-1 shown in FIG. 17 is a star-shaped sticker of for example area 7.5 square centimeters. The portion 500-2 of the letters "Long Life" on the surface of this security label 500-1 is an overt recording recorded with a color-change ink containing for example liquid-crystal material. This overt recording 500-2 is printed with for example an offset type printing device. Also, the portion 500-3 of the letters "E, P, O, O, N" indicated by broken lines is a covert recording printed with an offset type printing device using for example fluorescent ink. An adhesive layer, not shown, is provided on the back face of this security label 500-1. In addition, cuts 500-4 are provided as shown at two recessed corner portions of this security label 500-1.

While embodiments of the present invention have been described above, these are given by way of example for description of the present invention and it is not intended that the scope of the present invention should be restricted solely to these embodiments. The present invention can therefore be put into practice in various other modes without departing from the essence thereof.

A recorded article according to the present invention may be used to prevent counterfeiting of a product or to check the genuineness or thereof, by being applied to the product itself, which may be of various types manufactured of various materials such as paper, plastics, metal or wood, or to the product packaging or ancillary articles such as guarantees associated with the product. Also, a security label according to the present invention may be utilized for prevention of product counterfeiting or checking of genuineness, by being stuck onto products of various types as described above, the packaging of these products or ancillary articles associated with these products.

The invention claimed is:

1. A method of ascertaining genuineness of a recorded article comprising an underlying layer having first and second regions on both of which patterns are formed and a liquid-crystal ink layer possessing circular polarization dichroism which coats said first region of the underlying layer but does not cover said second region of said underlying layer, said method comprising the steps of:

observing said recorded article through an anticlockwise circularly polarized plate to determine whether said pattern on said first region of said underlying layer is invisible, whether said pattern on said second region of said underlying layer is visible, and whether said first and said second regions are distinguished by different colors; and observing said recorded article through a clockwise circularly polarized plate to determine whether said patterns on said first and said second regions of said underlying layer are both visible and whether said patterns of said first and said second regions appear with a same color.

* * * * *

UNITED STATES PATENT AND TRADEMARK OFFICE
CERTIFICATE OF CORRECTION

PATENT NO. : 7,408,630 B2
APPLICATION NO. : 11/286223
DATED : August 5, 2008
INVENTOR(S) : Hiroto Nakamura et al.

It is certified that error appears in the above-identified patent and that said Letters Patent is hereby corrected as shown below:

Cover Page,
    at (62) Related U.S. Application Data, after "Division of application no. 10/469,282, filed on Aug. 28, 2003", add --, filed as a 371 of int'l. patent appln. no. PCT/JP02/13226, filed on Dec. 18, 2002--.

add --(30) Foreign Application Priority Data
    Dec. 20, 2001   (JP) . . . . . . 2001-387116
    June 26, 2002  (JP) . . . . . . 2002-186721--.

Column 1,
    line 8, after "Aug. 28, 2003", add --, filed as a 371 of int'l. patent appln. no. PCT/JP02/13226, filed on December 18, 2002--.

Signed and Sealed this

Fourteenth Day of October, 2008

JON W. DUDAS
*Director of the United States Patent and Trademark Office*